United States Patent [19]

Fruehwirth

[11] Patent Number: Plant 7,726

[45] Date of Patent: Nov. 26, 1991

[54] POINSETTIA PLANT 'C-27 PINK'

[75] Inventor: Franz Fruehwirth, Encinitas, Calif.

[73] Assignee: Paul Ecke Ranch, Inc., Encinitas, Calif.

[21] Appl. No.: 528,237

[22] Filed: May 24, 1990

[51] Int. Cl.[5] ..... A01H 5/00

[52] U.S. Cl. ..... Plt./86

[58] Field of Search ..... Plt./86, 86.1, 86.3

*Primary Examiner*—Howard J. Locker

*Attorney, Agent, or Firm*—Arnold, White & Durkee

[57] ABSTRACT

Poinsettia 'C-27 Pink' is a stiff-stemmed, vigorous plant with bright pink, erect flower bracts. Cultivar 'C-27 Pink', is a sport of the red bracted 'C-27' (U.S. Plant Pat. No. 7,235). 'C-27 Pink', like its parent 'C-27', is unique because the flower bracts remain erect and do not droop even after commercial shipping and handling or as the flowers mature. It always looks "fresh" which adds to its beauty and increases its value as a consumer product. Poinsettia 'C-27 Pink' has the same flowering response time and cultural requirements as its parent 'C-27'.

1 Drawing Sheet

BACKGROUND OF THE NEW PLANT

This new Poinsettia cultivar originated as a sport of a 'C-27' (U.S. Plant Pat. No. 7,235) in a greenhouse in Encinitas, Calif. It was selected from many plants because of its large, erect and bright pink flower bracts and stiff stems; traits which distinguish it from other poinsettia cultivars and seem to make it a desirable plant for commercial greenhouse production. After selection, stem cuttings of this plant were vegetatively reproduced for test purposes in Encinitas, Calif., and clones of the plant were subjected to successive generations of vegetative propagation which demonstrated that its distinctive characteristics hold true from generation to generation.

DESCRIPTION OF THE PHOTOGRAPHS

Poinsettia 'C-27 Pink' is illustrated in the accompanying color photographs. The upper photo is a side view of three unpinched 'C-27 Pink' plants, in a 14 cm. pot. The lower photo is a top view of the 'C-27 Pink' plants showing flower and bract formation.

DESCRIPTION OF THE PLANT

The following is a detailed description of this new poinsettia as observed in my greenhouse in Encinitas, Calif., during December 1989. Recorded observations from flowering plants, grown as 3 unpinched plants per pot, were observed. The pot was 14 cm. in diameter and 11 cm. in height. Color designations were compared to the 1986 edition of R.H.S. Colour Chart, First published in 1966 by the Royal Horticultural Society, London, England.

THE PLANT

Origin: Sport of 'C-27' (U.S. Plant Pat. No. 7,235).

Classification:

*Botanic.*—*Euphorbia pulcherrima* Willd.

*Common name.*—Poinsettia.

*Cultivar name.*—'C-27 Pink'.

Form: Shrub.

Height: Medium.

Growth habit: As a single stemmed plant, upright and vigorous. The application of a chemical growth retardant may be needed to restrict height for commercial pot plant production. Observations of 3 plants in a pot with an overall height of 45 cm. and an overall width of 52 cm. were made. The bract diameter of individual flowers was 34 cm.

Branching: Poinsettia 'C-27 Pink' like its parent plant 'C-27', is not a self-branching cultivar. Branching can be enhanced by removal of the stem tip. Then, several flowering branches will develop on a single plant. Commercially 'C-27 Pink' is valuable for those who wish to market single-stemmed plants with large, showy bracts. If pinched, one could expect 3–5 axillary branches to develop.

Growth rate: Very fast. Rooting of stem cuttings occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being about 12–14 cm. long and about 9–11 cm. wide with leaf petioles about 5–6 cm. long.

*Leaf shape.*—Typical leaves are ovate with obtuse bases and acuminate tips. Leaf margins are sometimes lobed with one or two indentations of each side of the leaf blade.

*Color.*—Upper side — Green, near R.H.S. 137A. Under side — Green, near R.H.S. 147B.

*Retention.*—The foliage lasts fairly well even under low light intensities in the consumer's home.

Bracts: Generally there are 18–24 bright pink bracts of various sizes with reddish veins subtending the cyathia. The smaller, inner bracts are usually darker pink than the older mature bracts. The primary bracts have blades typically 17–18 cm. long and 10–12 cm. wide with petioles about 3 cm. long. Bract attitude is similar for both 'C-27 Pink' and its parent 'C-27'.

*Shape.*—Bracts are mostly ovate with acute bases and acuminate tips. Primary bracts are lobed with two indentations on either side of the bract. Secondary bracts are elliptic to obovate and have mostly entire margins.

*Color.*—Upper side — Bright pink, near R.H.S. 51C. Small inner bracts near R.H.S. 51B. Reddish somewhat obscure veins near R.H.S. 45B. Under side — Pink, near R.H.S. 51D.

Flowers: Generally, 15–18 cyathia (flowers) are present when the plant is in full bloom. Each cyathium is about 8 mm long and about 5 mm wide, green in color and fringed with dark pink at the distal end. One bright yellow nectar cup protrudes from the side of each cyathium. The flower pedicel is also green and about 5–6 mm in length. The stamens protruding from the cyathia are pink.

What is claimed is:

1. A new and distinct Poinsettia cultivar, substantially as herein shown and described, characterized by its large, erect and bright pink flower bracts and stiff stems.

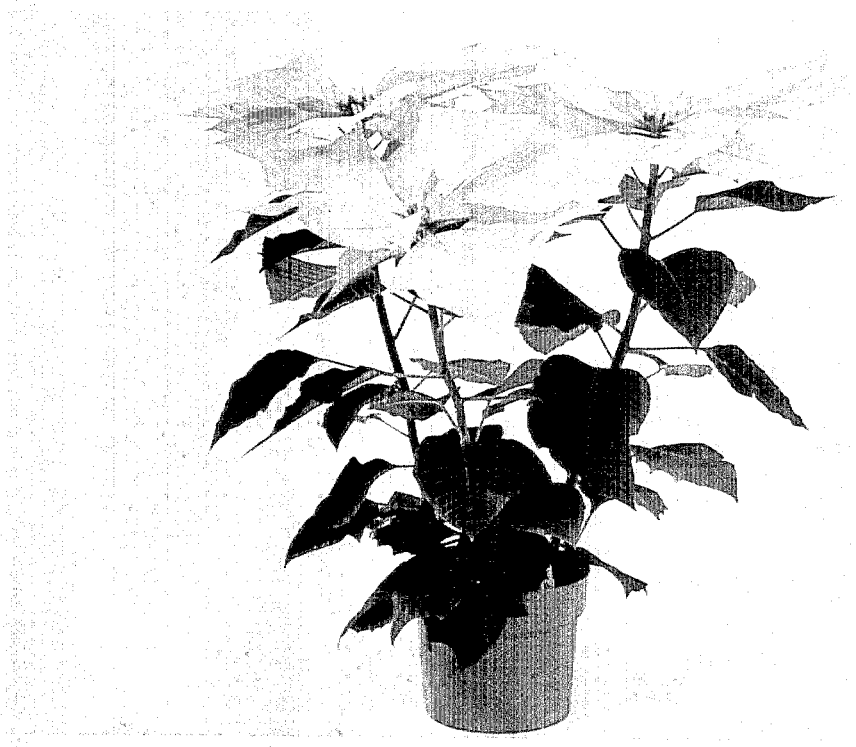
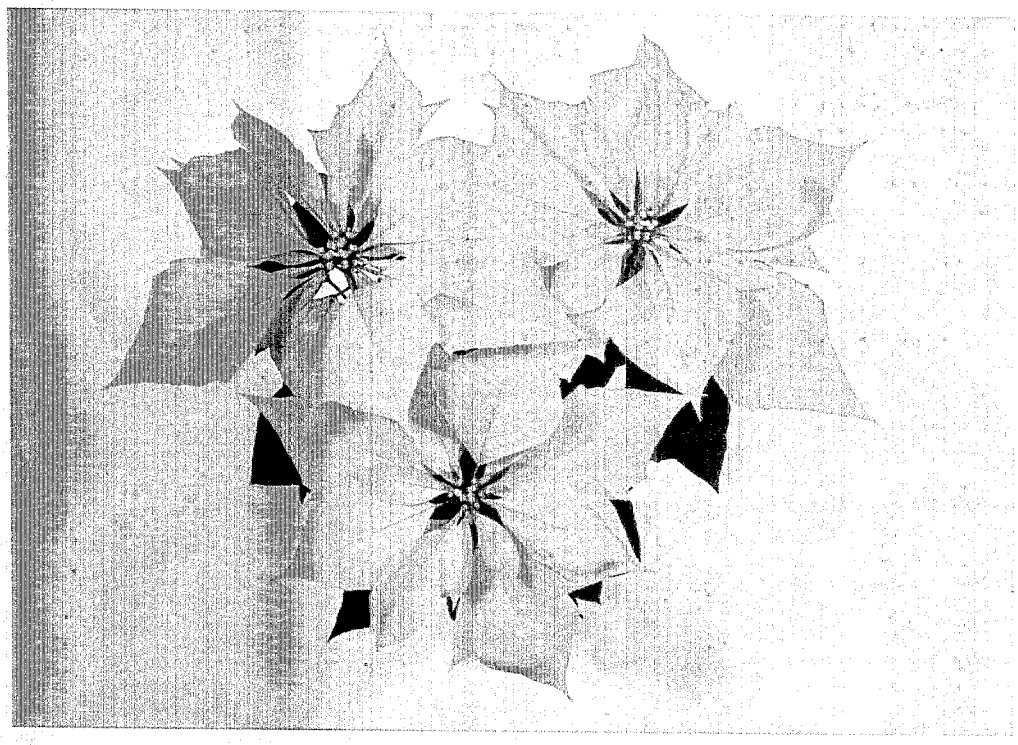

* * * * *